(12) United States Patent
Wieslander et al.

(10) Patent No.: US 10,894,119 B2
(45) Date of Patent: Jan. 19, 2021

(54) SYSTEM FOR PROPORTIONING FLUIDS

(71) Applicant: GAMBRO LUNDIA AB, Lund (SE)

(72) Inventors: Anders Wieslander, Lund (SE); Olof Jansson, Vellinge (SE); Ola Carlsson, Lund (SE); Sture Hobro, Lund (SE); Karin Sandin, Sodra Sandby (SE); Simon Enarsson, Lund (SE)

(73) Assignee: Gambro Lundia AB, Lund (SE)

( * ) Notice: Subject to any disclaimer, the term of this patent is extended or adjusted under 35 U.S.C. 154(b) by 0 days.

(21) Appl. No.: 16/095,088

(22) PCT Filed: May 5, 2017

(86) PCT No.: PCT/EP2017/060769
§ 371 (c)(1),
(2) Date: Oct. 19, 2018

(87) PCT Pub. No.: WO2017/191301
PCT Pub. Date: Nov. 9, 2017

(65) Prior Publication Data
US 2019/0151526 A1    May 23, 2019

(30) Foreign Application Priority Data

May 6, 2016 (SE) ...................................... 1650611

(51) Int. Cl.
*A61K 9/00*    (2006.01)
*A61M 1/28*    (2006.01)
(Continued)

(52) U.S. Cl.
CPC ............. *A61M 1/287* (2013.01); *A61K 31/19* (2013.01); *A61K 31/194* (2013.01);
(Continued)

(58) Field of Classification Search
CPC ...................................................... A61M 1/287
See application file for complete search history.

(56) References Cited

U.S. PATENT DOCUMENTS 5,344,392 A   9/1994  Senninger
5,827,820 A   10/1998 duMoulin
(Continued)

FOREIGN PATENT DOCUMENTS

EP   1008341    6/2000
EP   2965747    1/2016
(Continued)

OTHER PUBLICATIONS

PCT Search Report and Written Opinion for PCT/EP2017/060769 dated Jul. 18, 2017 (15 pages).
(Continued)

*Primary Examiner* — Paul W Dickinson
(74) *Attorney, Agent, or Firm* — Mueting Raasch Group (57) ABSTRACT

The present invention concerns a system for preparing a ready-to-use peritoneal dialysis fluid. The system comprises a) a proportioning device; b) at least one source of water; c) at least one source of first concentrate adapted for connection with a) and b), d) at least one source of second concentrate adapted for connection with a) and b), and optionally, e) at least one source of further concentrate adapted for connection with a) and b), wherein the first concentrate comprises glucose and has a pH of between 1.5 and 4, and wherein the second concentrate comprises a physiologically acceptable buffer and has a pH of between 5.5 and 9.0.

29 Claims, 3 Drawing Sheets

(51) Int. Cl.
    *A61M 1/16*     (2006.01)
    *A61K 31/19*     (2006.01)
    *A61K 31/194*     (2006.01)
    *A61K 31/7004*     (2006.01)
    *A61K 33/14*     (2006.01)
    *A61K 33/20*     (2006.01)

(52) U.S. Cl.
    CPC .......... *A61K 31/7004* (2013.01); *A61K 33/14* (2013.01); *A61K 33/20* (2013.01); *A61M 1/1696* (2013.01); *A61M 2202/0488* (2013.01)

(56) References Cited

U.S. PATENT DOCUMENTS

| | | | |
|---|---|---|---|
| 6,020,007 | A | 2/2000 | Veech |
| 6,610,206 | B1 | 8/2003 | Callan |
| 6,689,393 | B1 | 2/2004 | Knerr |
| 2005/0020507 | A1 | 1/2005 | Zieske |
| 2005/0276868 | A1 | 12/2005 | DeGreve |

FOREIGN PATENT DOCUMENTS

| | | |
|---|---|---|
| WO | WO 92/05814 | 4/1992 |
| WO | WO 01/19413 | 3/2001 |
| WO | WO 2004/105730 | 12/2004 |
| WO | WO 2005/011631 | 2/2005 |
| WO | WO 2006/083653 | 8/2006 |
| WO | WO 2012/129501 | 9/2012 |
| WO | WO 2013/141896 | 9/2013 |

OTHER PUBLICATIONS

PCT Search Report and Written Opinion for PCT/EP2017/060771 dated Aug. 7, 2017 (10 pages).

Himmele et al., "A New Neutral-pH Low-GDP Peritoneal Dialysis Fluid", *Peritoneal Dialysis International*, vol. 32, No. 4, pp. 444-452, Mar. 2012.

Erixon et al., "How to Avoid Glucose Degradation Products in Peritoneal Dialysis Fluids", *Peritoneal Dialysis International*, vol. 26, pp. 490-497, Jul. 2006.

SYSTEM FOR PROPORTIONING FLUIDS

This application is a U.S. National Stage Application of International Application No. PCT/EP2017/060769, filed 5 May 2017 and published in English on 9 Nov. 2017 as International Publication No. WO 2017/191301 A1, which claims the benefit of priority under 35 U.S.C. § 119(a) of Swedish Patent Application No. 1650611-5 filed 6 May 2016, each of which are incorporated herein by reference in their entireties.

TECHNICAL FIELD

The present invention relates to the field of fluid compounding for preparing fluids particularly for the treatment of renal insufficiency. More specifically, it relates to a system for the treatment of renal insufficiency configured for compounding finished fluids from one, two or more concentrates for use as a dialysis fluid. In particular, the invention may be used for preparing fluids for peritoneal dialysis, particularly for preparing fluids on-site.

BACKGROUND

Patients with acute or chronic renal insufficiency may need supporting treatment in the form of dialysis for the removal of waste substances and excess of fluid from the body. Dialysis is a process to remove fluid and waste products from the patient by the use of diffusional or convective transport. Various dialysis techniques with associated dialysis fluids may be differentiated. Which dialysis technique to use, depends on the patient needs, treatment demands and available resources.

There are different dialysis treatments available, hemodialysis (HD), hemofiltration (HF), hemodiafiltration (HDF), and peritoneal dialysis (PD). The in-center hemodialysis patient normally receives dialysis therapy 3-5 hours, about three times per week. The dialysis therapy is usually performed at a dialysis center, although home dialysis is also possible. When home dialysis is performed the patient is free to perform dialysis more frequently and typically also in a more gentle treatment with longer duration, i.e. 4-8 hours per treatment and 5-7 treatments per week. The dose and treatment duration may be adjusted to each patient's demands and needs.

In the case of patients suffering from acute renal insufficiency, patients may be treated with either HD or PD, special kind of HD is continuous renal replacement therapy (CRRT), a continuous treatment throughout the entire day, and in some cases for several weeks. Alternatively, patients may also be treated with ordinary HD treatment (intermittent treatment) or a slower form of HD called slow extended dialysis (SLED).

Peritoneal dialysis is one available dialysis techniques for patients having renal failure. During this treatment sterile peritoneal dialysis fluids are infused in the peritoneal cavity of the patient via a catheter inserted through the abdominal wall. In peritoneal dialysis, the peritoneum serves as the dialysis membrane. An osmotic pressure gradient is applied by the addition of an osmotic agent to the dialysis fluid which will cause fluid removal from the blood. The amount of fluid removed during the dialysis treatment depends on the concentration of the osmotic agent chosen in the fluids used, the higher concentration, the larger amount of fluid is removed.

There are different methods of peritoneal dialysis treatment available, such as Continuous Ambulatory Peritoneal dialysis (CAPD), and Automated Peritoneal Dialysis (APD).

In automated peritoneal dialysis, an automated cycler is used to infuse and drain dialysis fluid. This form of treatment may be done automatically at night while the patient sleeps. The cycler measures the amount of fluid infused and the amount removed to compute the net fluid removal. The treatment sequence usually begins with an initial drain cycle to empty the peritoneal cavity of dialysate (also called spent dialysis fluid). The cycler then performs a series of fill, dwell, and drain cycles, typically finishing with a fill cycle.

Peritoneal dialysis generally requires large volumes of dialysis fluids. Generally, at each application, or exchange, a given patient will infuse 0.5 to 3 liters of dialysis fluid into the peritoneal cavity. The fluid is allowed to dwell for approximately 3-4 hours, at which time it is drained out and exchanged for fresh fluid. Generally, four such exchanges are performed daily. Approximately 8 to 20 liters of dialysis fluid is required per day, 7 days a week, 365 days a year for each patient.

The peritoneal dialysis fluids have traditionally been provided in bags, often as 1.5 L, 2 L, 3 L, 5 L, or 6 L bags, and being terminally sterilized. Shipping and storage of the sheer volume of fluids required is both tremendously inconvenient and expensive. Further, for the patient, the repeated connection and disconnection of so many fluid containers creates a substantial risk of microbiological contamination at the point of connection. Additionally, tremendous amounts of waste material, in form of empty containers and packaging, and their proper disposal are increasingly becoming a concern.

There is a desire to reduce these concerns and solve the problems with large amounts of dialysis fluids. The present invention provides a fluid solution to the problem by providing a system wherein small volumes of concentrated dialysis fluids are combined and diluted with purified water at the point of care, i.e. close to the patient. The concentrates of components for preparing the ready-to-use peritoneal dialysis fluid are each provided in volumes of about 1 L and will replace the 8-55 L of peritoneal dialysis fluid commonly used today. Further, there is a need to provide on-site preparation of fluids for peritoneal dialysis fluids, to be used in APD or CAPD, and provide treatments fulfilling requirements of safety, sterility and accuracy to a larger extent than present available treatments.

WO2013/1141896 describes a system, device and method for peritoneal dialysis. The system may include controller means which are configured to compare a conductivity of a batch of fluid.

WO2012/129501 describes peritoneal dialysis systems, devices and methods, including a prescription driven dialysis fluid preparation.

An apparatus for proportioning and compounding concentrates into a solution for use as a kidney dialysis solution is known from U.S. Pat. No. 5,344,392.

Also a concentrate to be used in this apparatus is described therein. The concentrate 1 contains the following:

11.34 g/100 ml NaCl–($M_w$=58.44 g/mol); 1940 mM 7.84 g/100 ml sodium lactate ($M_w$=112.06 g/mol); 700 mM 514 mg/100 ml calcium chloride ($M_w$ (CaCl$_2$*2H$_2$O=147.01 g/mol); 35.0 mM 304 mg/100 ml magnesium chloride ($M_w$=203.31 g/mol (hexahydrate)); 14.95 mM.

The concentrate has a pH of approximately 6.4.

Concentrate 1 is intended to be mixed with concentrate 2 comprising a solution of 50% dextrose. The resulted solution is for dilution 1 to 20 (1+19), to obtain a ready to use peritoneal dialysis fluid is obtained.

However, since the pH of the glucose solution is undefined, the solution described is considered to generate an non-acceptable level of glucose degradation products (GDPs). Sterilization of glucose containing fluids is challenging as during the sterilization process some of the glucose degrades and forms cytotoxic GDPs. A further need is to provide a system with concentrates suitable for on-site preparation of peritoneal dialysis fluid, having sufficient storage stability and biocompatibility, and resulting in a ready-to-use pH close to physiological/neutral to reduce infusion pain, which is clean of impurities including GDPs and precipitates, is microbiologically safe, and provides an osmotic gradient fitting the patient's need for dialysis and/or ultrafiltration.

SUMMARY OF THE INVENTION

An object of the invention was to provide a system for preparing a ready-to-use peritoneal dialysis fluid.

In one embodiment of the invention a system is provided, a system comprising,
a) a proportioning device;
b) at least one source of water adapted for connection with said proportioning device;
c) at least one source of first concentrate adapted for connection with a) and b);
d) at least one source of second concentrate adapted for connection with a) and b);
optionally, e) at least one source of further concentrate adapted for connection with a) and b), and is further defined by that said first concentrate comprises glucose and has a pH of between 1.5 and 4, for example a pH of between 2 and 3.5, or a pH of between 2.2 and 3.2; and said second concentrate comprises a physiologically acceptable buffer; and has a pH of between 5.5 and 9.0.

The ready-to-use peritoneal fluid may also prepared to have a pH between 5.5-8, for example pH between 6.5-7.5, or between 6.8-7.5.

In one embodiment of the invention the system comprises said first concentrate comprising glucose which has a pH of between 1.5 and 4 or a pH of between 2 and 3.5 or a pH between 2.2 and 3.0; said second concentrate comprises a physiologically acceptable buffer which has a pH of between 6.0 and 8.5.

The prepared ready to use peritoneal dialysis fluid has the following content:

| | |
|---|---|
| Sodium (Na+) | 100-140 mM |
| Potassium (K+) | 0-4 mM |
| Calcium (Ca$^{2+}$) | 0-2 mM |
| Magnesium (Mg$^{2+}$) | 0-0.75 mM |
| Lactate | 0-40 mM |
| Bicarbonate | 0-35 mM |
| Glucose | 0-5%. |

In one embodiment of the invention the physiologically acceptable buffer is selected from the group comprising acetate, lactate, citrate, pyruvate, carbonate, bicarbonate, and amino acid buffer; or mixtures thereof.

In one embodiment of the invention the physiologically acceptable buffer is lactate.

In one embodiment of the invention the physiologically acceptable buffer is bicarbonate.

In another embodiment of the invention the physiologically acceptable buffer is a mixture of lactate and bicarbonate.

In one embodiment of the invention said first concentrate further comprises at least one of electrolyte selected from the group comprising sodium, calcium, magnesium, and optionally potassium.

In one embodiment of the invention said second concentrate further comprises at least one of electrolyte selected from the group comprising sodium, calcium, magnesium, and optionally potassium.

In another embodiment of the invention said further concentrate comprises at least one of electrolyte selected from the group comprising sodium, calcium, magnesium, and optionally potassium.

A system for preparing ready-to-use peritoneal fluids having flexibility and capability to profiling of electrolytes, for example of calcium is provided by the present invention.

In another embodiment of the invention, said further concentrate comprises a physiologically acceptable buffer selected from the group comprising acetate, lactate, citrate, pyruvate, carbonate, bicarbonate, and amino acid buffer; or mixtures thereof. This will give further flexibility for preparing the peritoneal dialysis fluid.

In another embodiment does said first concentrate and said second concentrate comprise calcium, and at least one further electrolyte selected from the group comprising sodium, magnesium, and optionally potassium.

In another embodiment said second concentrate and said further concentrate comprises calcium and at least one further electrolyte selected from the group comprising sodium, magnesium, and optionally potassium.

In another embodiment said first concentrate and said second concentrate comprise calcium, and at least one further electrolyte selected from the group comprising sodium, magnesium, and optionally potassium; and optionally said further concentrate comprises at least one electrolyte selected from the group comprising sodium, calcium, magnesium, and optionally potassium.

A system comprising calcium, and optionally magnesium, in said first concentrate simultaneously as in said second concentrate provides a system wherein profiling of calcium is achieved. The flexibility of calcium may vary within wider range than in a system where calcium is present only in one of the concentrates, first, second or the further concentrate. By reducing the concentration of calcium, and optionally of magnesium, in the said second concentrate, thus the lactate containing concentrate, the stability of said second concentrate may be improved.

Another embodiment of the present invention is a system wherein said first concentrate and/or said second concentrate and/or said further concentrate are terminal sterilized.

In one embodiment of the invention a system is provided,
a system comprising,
a) a proportioning device;
b) at least one source of water adapted for connection with said
proportioning device;
c) at least one source of first concentrate adapted for connection with a) and b), and being terminal sterilized;
d) at least one source of second concentrate adapted for connection with a) and b), and being terminal sterilized; optionally, e) at least one source of further concentrate adapted for connection with a) and b), and being terminal sterilized, and is further defined by that said first concentrate comprises glucose and has a pH of between 1.5 and 4, for example a pH of between 2 and 3.5, or a pH of between 2.2 and 3.2; and said second concentrate comprises a physiologically acceptable buffer; and has a pH of between 5.5 and 9.0, for example between 6.0 and 8.5.

The system as described herein includes one or more sources of water, preferably to provide purified water. By terminal sterilization of the first concentrate, the second concentrate, and/or the further concentrate it is possible to provide peritoneal dialysis fluid of a very high quality.

In one embodiment of the invention said second concentrate requires dilution with water and first, and optionally further concentrate. It is intended to be diluted approximately 1:10 to approximately 1:40; of between approximately 1:10 to 1:33, also denoted as 10×, 20×, 25×, 30×, 33×, 35×, and 40×.

In another embodiment said first concentrate comprises glucose; has pH of between 1.5 and 4; for example a pH of between 2 and 3.5, such as pH between 2.2 and 3.0, or pH between 2.2 and 2.8, and said second concentrate comprises sodium lactate, calcium chloride, and magnesium chloride; has a pH of between 5.5 and 8.5, for example pH between 6.5 and 8.5, or between pH 6.8 and 8.5; and optionally at least one of said first and said second concentrate is terminal sterilized, and admixed to form a ready-to-use peritoneal dialysis fluid as herein described.

More specifically, the ready-to-use peritoneal dialysis fluid contains the following:

| | |
|---|---|
| Sodium (Na$^+$) | 100-140 mM, preferably 132 mM |
| Potassium (K$^+$) | 0-4 mM |
| Calcium (Ca$^{2+}$) | 0-2 mM, preferably 0.5-2 mM; particularly 1.25-1.75 mM; |
| Magnesium (Mg$^{2+}$) | 0-0.75 mM, preferably 0.25-0.50 mM: |
| Lactate | 0-45 mM, preferably 0-40 mM, more preferably 0, 30, 35, or 40 mM |
| Glucose | 0-5%; 1.5-5% |

In another embodiment said first concentrate comprises glucose; have pH of between 1.5 and 4; pH of between 2 and 3.5; pH of between 2.2 and 2.8; said second concentrate comprises sodium bicarbonate, sodium chloride, and optionally sodium lactate; and has a pH of between 6.0 and 8.5; and said further concentrate comprises calcium chloride, magnesium chloride, and optionally lactic acid; and optionally, at least one of said first and second concentrate is terminal sterilized.

In another embodiment of the present invention said first concentrate has a water activity ($a_w$) of less than 0.95, and a pH<3.2.

Another embodiment of the invention is said second concentrate has a water activity ($a_w$) equal or less than 0.89, for example less than 0.85, or less than 0.8.

In another embodiment said first concentrate comprises glucose and has a conductivity of more than 100 µS/cm and pH between 1.5 and 3, more specifically, said first concentrate has a conductivity of more than 400 µS/cm, and pH 2.3. More specifically, said first concentrate comprises glucose and has a conductivity of more than 100 µS/cm, pH of between 1.5 and 3, said second concentrate comprises a physiologically acceptable buffer, and optionally at least one electrolyte selected from the group comprising sodium, calcium, magnesium, and optionally potassium, and has a pH of between 6.5 and 8.5.

With a first concentrate comprising glucose, having a conductivity of more than 100 µS/cm, the possibility to discern the concentrate is provided. Thus, it is possible to identify and discern the glucose containing concentrate from other concentrates included in the system and the said source of water.

Another advantage, with the present invention is that it is possible to provide a great flexibility in the glucose concentration in that fluid. When comparing with the option wherein sodium ions are added to the glucose concentrate greater flexibility is provided. The amount of sodium ions in the ready to use peritoneal dialysis fluid is restricted by the limits in the European Pharmacopoeia (±2.5%). Therefore, by avoiding sodium ions in the glucose concentrate the flexibility of changing and adjusting the glucose concentration is greater.

In one embodiment said first concentrate comprising glucose, further comprises a strong acid; preferably selected from hydrochloric acid (HCl) and organic acids. Examples of organic acids are citric acid, acetic acid etc.

In another embodiment said first concentrate further comprises one or more electrolytes selected from the group consisting of chloride and sodium.

In one embodiment said first concentrate comprises glucose and has a conductivity of more than 100 µS/cm at pH between 1.5 and 3; said second concentrate comprises sodium bicarbonate, sodium chloride, and optionally sodium lactate; and has a pH of between 6.5 and 8.5; and a third concentrate comprises calcium chloride, magnesium chloride, and optionally lactic acid. Optionally, at least one of the concentrates included in this embodiment is sterilized, preferably terminal sterilized.

In one embodiment said first concentrate comprises glucose, has pH of between 1.5 and 4, for example between 2 and 3.5, such as between 2.4 and 2.8; said second concentrate comprises the physiologically acceptable buffer lactate; calcium as an electrolyte, and optionally one or more electrolytes selected from the group comprising sodium, magnesium, and potassium; citrate in an amount having a stabilizing effect, and has a pH of between 6.0 and 8.5.

Particularly, the concentration of citrate is up to 10 mM. However, the concentration of citrate may be adjusted with the dilution factor of the concentrate. An example is citrate concentration of 10 mM, dilution factor of 1:40, and concentration of calcium of 50 mM in said second concentrate comprising lactate. Another example is citrate concentration of 10 mM, dilution factor of 1:20, and concentration of calcium of 35 mM said second concentrate comprising lactate.

A low amount of citrate is added to said further concentrate with the purpose to stabilize the pH of the concentrate and the ready-to-use fluid. The addition of citrate to the calcium containing fluid limits the risk of precipitation of calcium lactate. By addition of citrate the particle formation might be reduced. Furthermore, the pH of the ready-to-use peritoneal dialysis fluid is closer to physiological pH, or neutral, with the addition of citrate.

BRIEF DESCRIPTION OF THE DRAWINGS

FIG. 1 provides scheme 100 showing a system for preparing a ready to use peritoneal dialysis fluid. A container 10 comprising a first concentrate and a container 12 comprising a second concentrate are each connected to a proportioning device 16 for mixing by conduits. A source 14 of purified water is also connected to the mixer 16 by a conduit. The proportioning device 16 is controlled by a controller 18 based on input from a user interface 20. Depending on such user input and control signals from the controller 18, the proportioning device 16 receives specific amounts of first and optionally second concentrates as well as water from said sources 10, 12, 14, and produces a ready-to-use peritoneal dialysis fluid that is delivered through output/container 22.

DEFINITIONS

The term "first concentrate" means herein the source of glucose. The source may be provided as fluid concentrate or in form of dry powder concentrate.

The term "second concentrate" means herein the source of physiologically acceptable buffer. Examples of physiologically acceptable buffers are acetate, lactate, citrate, pyruvate, carbonate, bicarbonate, and amino acid buffer, if not otherwise specified. Further, the buffers are intended to be in form of alkali, for example alkali lactate, and alkali bicarbonate, such as sodium lactate, and sodium bicarbonate.

The term "citrate" means citric acid or any salt thereof. The salt may be formed with sodium, magnesium or potassium. The sodium citrate may be present as trisodium citrate ("Na-cit"), disodium hydrogencitrate, or monosodium dihydrogencitrate.

The term "terminal sterilized" is herein intended to mean that the product is sterilized in its final package. The terminal sterilization may include heat sterilization and/or radiation sterilization, but is preferably heat sterilization effected in an autoclave at a temperature of at least 100° C., preferably at least 121° C.

The term "dilution" as used herein refers to the mixing of a small, measured sample with a large volume of, for example, sterile water, saline or other appropriate liquid called the diluent or a dilution blank. A single dilution is calculated as follows:

Dilution=volume of the sample/(total volume of the sample+diluent volume).

For example, the dilution of 1 mL into 9 mL equals: 1/1+9, which is the same as 1/10 which is written 1/10 or $10^{-1}$.

This can then be called a one to ten dilution.

DETAILED DESCRIPTION OF THE INVENTION

By the present invention a system for preparing a ready-to-use peritoneal dialysis solution is provided. The system comprises the following:

a) a proportioning device;
b) at least one source of water adapted for connection with said proportioning device;
c) at least one source of first concentrate adapted for connection with a) and b);
d) at least one source of second concentrate adapted for connection with a) and b).

The system may also, optionally, comprise at least one source of further concentrate adapted for connection with a) and b). The said first concentrate comprises glucose and have pH of between 1.5 and 4. For example, the pH is between 2 and 3.5, more specifically, pH is between 2.2 and 3.0. The said second concentrate comprises a physiologically acceptable buffer; and has a pH of between 5.5 and 9.0, for example between 6.5 and 9, 6.0 and 8.5 or 6.5 and 8.5.

The system described herein is suitable for preparing a ready-to-use peritoneal dialysis fluid. The peritoneal dialysis fluid may be prepared from a first concentrate together with a second concentrate, optionally with one or more further concentrates.

The system as is described herein comprises a proportioning device. In the proportioning device are the concentrates admixed, i.e. proportioned and compounded, to form a ready-to-use peritoneal dialysis fluid. With the system as defined herein there is provided an easy way to prepare the dialysis fluid for the peritoneal dialysis treatment. Less amount and less volumes of concentrates are to be handled in connection with the treatment of the patient.

As mentioned above, systems for peritoneal dialysis are described in WO2013/1141896 and WO2012/129501. Also proportioning devices are described therein. Further, there are proportioning devices commercially available, for example, AMIA (Baxter International Inc).

Further, the system described herein includes at least one water source. The water to be added to the concentrate(s) included in this production shall have a certain chemical and microbiological quality (defined in e.g. European Pharmacopoeia) suitable for its application.

Water to be included in the source of water should be within limits that are safe from a microbiological and chemical perspective; this water could for example be "purified water", "highly purified water", "ultrapure water", "water for injection" (WFI), "sterile WFI", "water for hemodialysis", "distilled water", "sterile purified water" and "water for pharmaceutical use".

The herein defined first concentrate, second concentrate, and further concentrate may be terminal sterilized before they are included in the system. By having sterilized concentrate, by for example terminal sterilization, included in the system these can be mixed with the water having the quality as defined above and a ready-to-use peritoneal dialysis fluid of high quality is provided. There is no requirement of sterilization of the ready-to-use peritoneal dialysis fluid. By the invention, it is possible to provide the ready-to-use peritoneal dialysis fluid close to the point of care.

Figure 1:
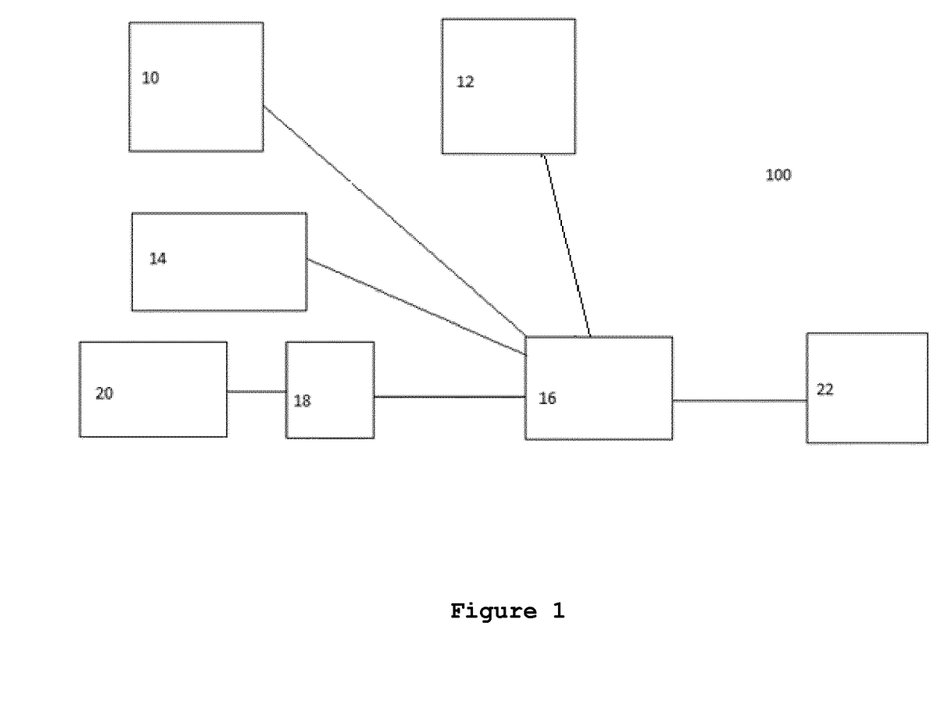
Figure 2:
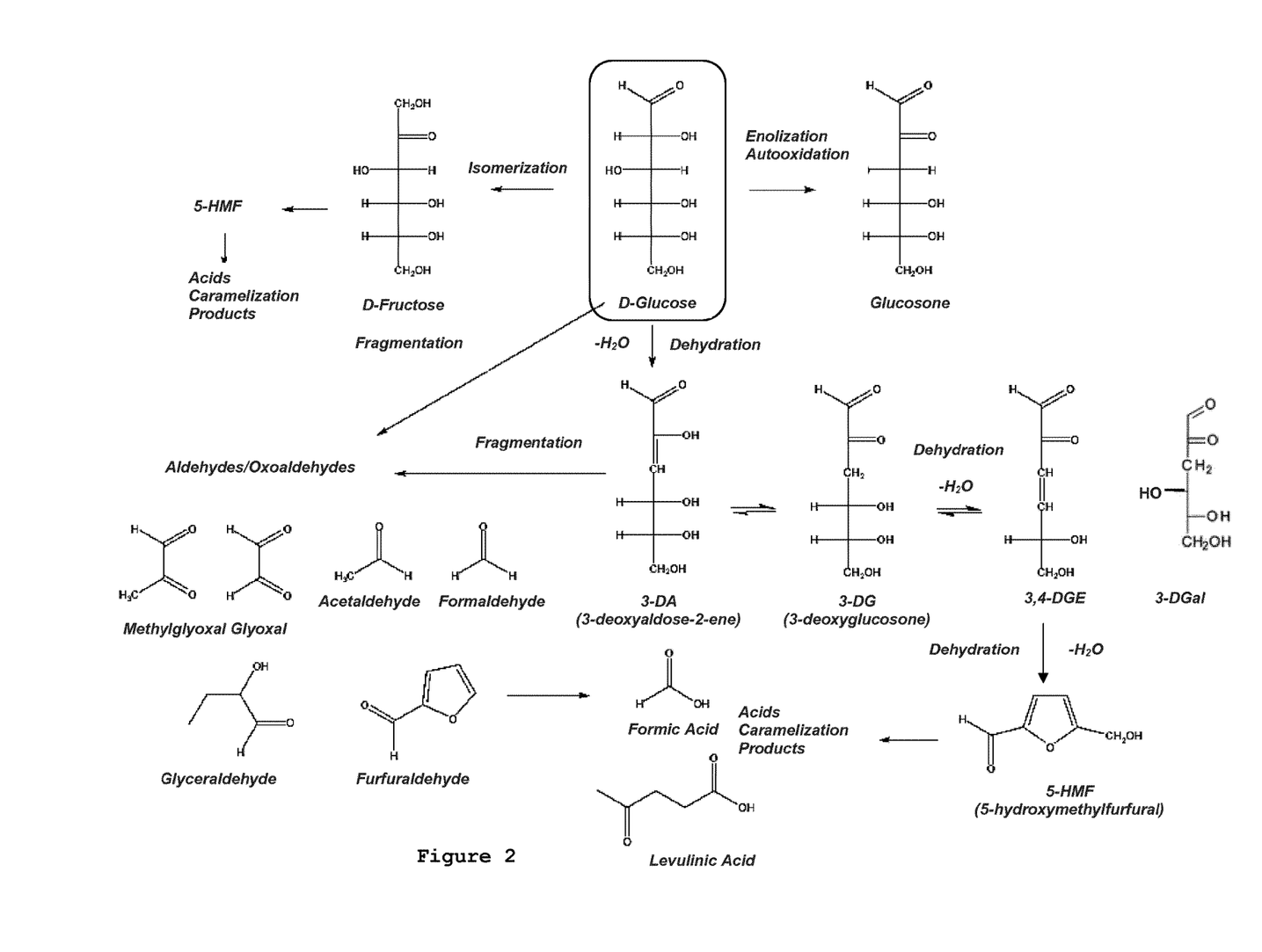
FIG. 2 represents known glucose degradation products and the degradation pathways starting from D-glucose.

FIG. 1 provides a scheme 100 showing a system for preparing a ready-to-use peritoneal dialysis fluid. A container 10 comprising a first concentrate and a container 12 comprising a second concentrate are each connected to a proportioning device 16 for mixing by conduits. In one embodiment (not shown in Figure), also a container comprising the further concentrate is included in the system. A source 14 of purified water is also connected to the mixer 16 by a conduit. The proportioning device 16 is controlled by a controller 18 based on input from a user interface 20. Depending on such user input and control signals from the controller 18, the proportioning device 16 receives specific amounts of first and optionally second concentrates as well as water from said sources 10, 12, 14, and produces a ready-to-use peritoneal dialysis fluid that is delivered through output/container 22.

By the system as herein defined, a ready-to-use peritoneal dialysis solution may have the following content:

| | |
|---|---|
| sodium (Na$^+$) | 100-140 mM |
| potassium (K$^+$) | 0-4 mM |
| calcium (Ca$^{2+}$) | 0-2 mM |
| magnesium (Mg$^{2+}$) | 0-0.75 mM |
| lactate | 0-40 mM |
| bicarbonate | 0-35 mM |
| glucose | 0-5% | is provided. The pH of the ready-to-use peritoneal dialysis solution is between 5.5-8, for example between 6.5-7.5, or between 6.8-7.5.

Further, preferably, the ready-to-use peritoneal dialysis fluid contains:

| | |
|---|---|
| sodium (Na$^+$) | 120-140 mM, more preferably 132 mM, |
| potassium (K$^+$) | 0-4 mM, for example 0, 1, 2, 3, 4 mM, |
| calcium (Ca$^{2+}$) | 0-2 mM, preferably 0.5-2 mM, particularly 1.25 mM, 1.5 mM, or 1.75 mM |
| magnesium (Mg$^{2+}$) | 0-0.75 mM, preferably 0.25-0.5 mM, for example 0.25, 0.3, 0.35, 0.4, 0.45, and 0.5, |
| lactate | 0-40 mM, preferably 0, 30, 35, or 40 mM, |
| bicarbonate | 0-35 mM, preferably 0, 30, 35 mM, |
| glucose | 0-5%. |

In another embodiment of the invention there is provided ready-to-use peritoneal dialysis fluid comprising a lactate and bicarbonte buffer. For example, the fluid has the following content:

| | |
|---|---|
| sodium (Na$^+$) | 100-140 mM, preferably 120-140 mM, more preferably 132 mM, |
| potassium (K$^+$) | 0-4 mM, for example 0, 1, 2, 3, 4 mM, |
| calcium (Ca$^{2+}$) | 0-2 mM, preferably 0.5-2 mM, particularly 1.25 mM, 1.5 mM, or 1.75 mM |
| magnesium (Mg$^{2+}$) | 0-0.75 mM, preferably 0.25-0.5 mM, for example 0.25, 0.3, 0.35, 0.4, 0.45, and 0.5, |
| lactate | 10 mM |
| bicarbonate | 25 mM |
| glucose | 0-5%. |

For example, the fluid has the following content:

| | |
|---|---|
| sodium (Na$^+$) | 100-140 mM, preferably 120-140 mM, more preferably 132 mM, |
| potassium (K$^+$) | 0-4 mM, for example 0, 1, 2, 3, 4 mM, |
| calcium (Ca$^{2+}$) | 0-2 mM, preferably 0.5-2 mM, particularly 1.25 mM, 1.5 mM, or 1.75 mM |
| magnesium (Mg$^{2+}$) | 0-0.75 mM, preferably 0.25-0.5 mM, for example 0.25, 0.3, 0.35, 0.4, 0.45, and 0.5, |
| lactate | 15 mM |
| bicarbonate | 25 mM |
| glucose | 0-5%. |

In another example, the fluid contains:

| | |
|---|---|
| sodium (Na$^+$) | 100-140 mM, preferably 120-140 mM, more preferably 132 mM, |
| potassium (K$^+$) | 0-4 mM, for example 0, 1, 2, 3, 4 mM, |
| calcium (Ca$^{2+}$) | 0-2 mM, preferably 0.5-2 mM, particularly 1.25 mM, 1.5 mM, or 1.75 mM |
| magnesium (Mg$^{2+}$) | 0-0.75 mM, preferably 0.25-0.5 mM, for example 0.25, 0.3, 0.35, 0.4, 0.45, and 0.5, |
| lactate | 15 mM |
| bicarbonate | 15 mM |
| glucose | 0-5%. |

The list of examples of ready-to-use peritoneal dialysis fluids is not exhaustive or intended to limit the present invention.

The first concentrate herein described comprises glucose, and is adjusted to pH 1.5-4. The concentrate is acidified by for example addition of hydrochloric acid (HCl). The concentrate may comprise 1.5-4 M glucose, for example between 1.5-3.9 M, or between 1.6-3.9 M. First concentrate may optionally contain 0-0.05 M calcium (Ca$^{2+}$), 0-0.01M magnesium (Mg$^{2+}$), and 0-0.05 M sodium (Na+).

The second concentrate herein described comprises a physiologically acceptable buffer, and optionally one or more electrolytes. The second concentrate may contain 1.0-5.5 M sodium (Na$^+$), 0-0.15 M calcium (Ca$^{2+}$), such as 0-0.12 M calcium (Ca$^{2+}$), 0-0.03 M magnesium (Mg$^{2+}$), 0-1.60 M lactate, 0-1.60 M bicarbonate. Optionally, the second concentrate contains 0-0.1 M potassium (K$^+$). Optionally, the second concentrate contains 0-15 mM citrate, such as 0-10 mM citrate.

A further concentrate may be included in the system herein described, the further concentrate may, for example, comprise 0-2 M sodium (Na$^+$), 0-0.06 M calcium (Ca$^{2+}$), and 0-0.15 M magnesium (Mg$^{2+}$).

Further the system comprises at least one source of second concentrate comprising a physiologically acceptable buffer. The buffer can be selected from the group comprising acetate, lactate, citrate, pyruvate, carbonate, bicarbonate, or mixtures thereof. The physiologically acceptable buffer can also comprise one or more amino acids, such as histidine, its isomers, polymers, and derivatives thereof. Example of histidine is L-histidine.

The concentrates included herein have a defined water activity. Water activity, or $a_w$, is the ratio of vapor pressure of H$_2$O in the product to vapor pressure of pure H$_2$O (P$_o$) at the same temperature. By defining and modifying the water activity of the concentrates higher resistance against microbiological growth can be obtained. The general limit for bacterial growth and proliferation is a water activity of 0.91, below that limit the growth of bacteria/microorganisms is slower. Therefore, it is an aim to provide a concentrate with a water activity that limits bacterial growth.

The concentrates having a defined water activity may be possible to use during an extended period of time ("extended use") in comparison with concentrates not having the defined water activity.

The first concentrate as herein described shall have a water activity ($a_w$) of less than 0.95, and a pH lower than 3.3, when used during an extended period of time.

The second concentrate as herein described shall have a water activity ($a_w$) of less than 0.9, preferably less than 0.89, for example less than 0.85, or less than 0.8.

As described above, there is a need to provide a system including concentrates suitable for on-site preparation of peritoneal dialysis fluid clean of impurities including GDPs. By the invention as described herein it is provided a system for providing ready-to-use peritoneal dialysis fluids having a concentration of glucose degradation product <20 μmol/L of 3,4-DGE, such as <15 μmol/L of 3,4-DGE, <10 μmol/L of 3,4-DGE, or <5 μmol/L of 3,4-DGE. In another embodiment of the invention, the ready-to-use peritoneal dialysis fluids having a concentration of glucose degradation product <8 μmol/L of glucosone, such as <5 μmol/L of glucosone, or <3 μmol/L of glucosone. In another embodiment of the invention, the ready-to-use peritoneal dialysis fluids having a concentration of glucose degradation product <17 μmol/L of 5-HMF, such as <14 μmol/L of 5-HMF, or <10 μmol/L of 5-HMF, or <8 μmol/L of 5-HMF. In another embodiment of the invention, the ready-to-use peritoneal dialysis fluids having a concentration of glucose degradation product <25 μmol/L of 3-DG, such as <20 μmol/L of 3-DG, or <15 μmol/L of 3-DG, or <10 μmol/L of 3-DG.

Another embodiment of the present invention is the system including a second concentrate as herein described, including a physiologically acceptable buffer, and optionally at least one electrolyte selected from the group comprising sodium, calcium, magnesium, and potassium, with the proviso that the second concentrate does not comprise the following composition:

11.34 g/100 ml NaCl (Mw=58.44 g/mol); 1940 mM
7.84 g/100 ml sodium lactate (Mw=112.06 g/mol); 700 mM
514 mg/100 ml calcium chloride (Mw (CaCl$_2$*2H$_2$O=147.01 g/mol); 35.0 mM
304 mg/100 ml magnesium chloride (Mw=203.31 g/mol (hexahydrate)) 14.95 mM,
with a pH of approximately 6.4.

In one embodiment of the invention a system is provided, a system comprising
a) a proportioning device;
b) at least one source of water adapted for connection with said
proportioning device;
c) at least one source of first concentrate adapted for connection with a) and b);
d) at least one source of second concentrate adapted for connection with a) and b);
optionally, e) at least one source of further concentrate adapted for connection with a) and b),
and is further defined by that said first concentrate optionally comprises glucose and has a pH of between 1.5 and 4, for example a pH of between 2 and 3.5, or a pH of between 2.2 and 3.2; and said second concentrate comprises a physiologically acceptable buffer; and has a pH of between 5.5 and 9.0.

The ready-to-use peritoneal fluid may also prepared to have a pH between 5.5-8.0, for example pH between 6.5-7.5, or between 6.8-7.5, or between 6.0-8.5.

EXAMPLES

By way of example, and not limitation, the following examples identify a variety of candidate concentrates to be used in the system for providing a final peritoneal dialysis fluid. These are presented in Example 1-18. Water activity has been tested of the concentrates and is presented in Examples 19-20. Stability of the fluids has been tested, present in Example 21-22. pH of the ready-to-use dialysis fluids have been measured, and is presented in Example 23-29. Tests of pH of the first concentrate before and after sterilisation have been performed, is presented in Example 30. Tests of pH of the second concentrate before and after sterilisation have been performed, is presented in Example 31. Example 32 provides data on the generation of glucose degradation products and their concentration in the ready to use solution.

Example 1

| Concentrate A1 | |
|---|---|
| Glucose | 2.775M |
| Hydrochloric acid | ad. pH 2.0-3.2 |
| Concentrate B1 | |
| Sodium chloride | 3.68M |
| Calcium chloride | 0.07M |
| Magnesium chloride | 0.01M |
| Sodium lactate | 1.60M |
| Sodium hydroxide | ad. pH 6.5-9.0 |

Mixed Solution Composition Example 1

| | | | | | |
|---|---|---|---|---|---|
| A (mL/L) | 0 | 30 | 50 | 80 | 100 |
| B (mL/L) | | | 25 | | |
| Na$^+$ (mM) | | | 132 | | |
| Mg$^{2+}$ (mM) | | | 0.25 | | |
| Ca$^{2+}$ (mM) | | | 1.75 | | |
| Cl$^-$ (mM) | | | 96 | | |
| Lactate (mM) | | | 40 | | |
| Glucose (mM) | 0 | 83.3 | 138.8 | 222.0 | 278 |

Example 2

| Concentrate A2 | |
|---|---|
| Glucose | 2.775M |
| Hydrochloric acid | ad. pH 2.0-3.2 |
| Concentrate B2 | |
| Sodium chloride | 3.22M |
| Calcium chloride | 0.0437M |
| Magnesium chloride | 0.00875M |
| Sodium lactate | 1.40M |
| Sodium hydroxide | ad. pH 6.5-9.0 |

Mixed Solution Composition Example 2

| | | | | | |
|---|---|---|---|---|---|
| A (mL/L) | 0 | 30 | 50 | 80 | 100 |
| B (mL/L) | | | 28.57 | | |
| Na$^+$ (mM) | | | 132 | | |
| Mg$^{2+}$ (mM) | | | 0.25 | | |
| Ca$^{2+}$ (mM) | | | 1.25 | | |
| Cl$^-$ (mM) | | | 95 | | |
| Lactate (mM) | | | 40 | | |
| Glucose (mM) | 0 | 83.3 | 138.8 | 222.0 | 278 |

Example 3

| Concentrate A3 | |
|---|---|
| Glucose | 2.775M |
| Hydrochloric acid | ad. pH 2.0-3.2 |
| Concentrate B3 | |
| Sodium chloride | 2.76M |
| Calcium chloride | 0.053M |

| | | | | | |
|---|---|---|---|---|---|
| Magnesium chloride | | | 0.008M | | |
| Sodium lactate | | | 1.20M | | |
| Sodium hydroxide | | | ad. pH 6.5-9.0 | | |

Mixed Solution Composition Example 3

| | | | | | |
|---|---|---|---|---|---|
| A (mL/L) | 0 | 30 | 50 | 80 | 100 |
| B (mL/L) | | | 33.3 | | |
| Na⁺ (mM) | | | 132 | | |
| $Mg^{2+}$ (mM) | | | 0.25 | | |
| $Ca^{2+}$ (mM) | | | 1.75 | | |
| $Cl^-$ (mM) | | | 96 | | |
| Lactate (mM) | | | 40 | | |
| Glucose (mM) | 0 | 83.3 | 138.8 | 222.0 | 278 |

Example 4

| Concentrate A4 | |
|---|---|
| Glucose | 2.775M |
| Hydrochloric acid | ad. pH 2.0-3.2 |
| Concentrate B4 | |
| Sodium chloride | 1.84M |
| Calcium chloride | 0.035M |
| Magnesium chloride | 0.005M |
| Sodium lactate | 0.80M |
| Sodium hydroxide | ad. pH 6.5-9.0 |

Mixed Solution Composition Example 4

| | | | | | |
|---|---|---|---|---|---|
| A (mL/L) | 0 | 30 | 50 | 80 | 100 |
| B (mL/L) | | | 50 | | |
| Na⁺ (mM) | | | 132 | | |
| $Mg^{2+}$ (mM) | | | 0.25 | | |
| $Ca^{2+}$ (mM) | | | 1.75 | | |
| $Cl^-$ (mM) | | | 96 | | |
| Lactate (mM) | | | 40 | | |
| Glucose (mM) | 0 | 83.3 | 138.8 | 222.0 | 278 |

Example 5

| Concentrate A5 | |
|---|---|
| Glucose | 2.775M |
| Hydrochloric acid | ad. pH 2.0-3.2 |
| Concentrate B5 | |
| Sodium chloride | 1.84M |
| Calcium chloride | 0.025M |
| Magnesium chloride | 0.005M |
| Sodium lactate | 0.80M |
| Sodium hydroxide | ad. pH 6.5-9.0 |

Mixed Solution Composition Example 5

| | | | | | |
|---|---|---|---|---|---|
| A (mL/L) | 0 | 30 | 50 | 80 | 100 |
| B (mL/L) | | | 50 | | |
| Na⁺ (mM) | | | 132 | | |
| $Mg^{2+}$ (mM) | | | 0.25 | | |
| $Ca^{2+}$ (mM) | | | 1.25 | | |
| $Cl^-$ (mM) | | | 96 | | |
| Lactate (mM) | | | 40 | | |
| Glucose (mM) | 0 | 83.3 | 138.8 | 222.0 | 278 |

Example 6

| Concentrate A6 | |
|---|---|
| Glucose | 2.775M |
| Calcium chloride | 0.010M |
| Magnesium chloride | 0.0032M |
| Hydrochloric acid | ad. pH 2.0-3.2 |
| Concentrate B6 | |
| Sodium chloride | 3.68M |
| Calcium chloride | 0.038M |
| Magnesium chloride | 0.010M |
| Sodium lactate | 1.60M |
| Sodium hydroxide | ad. pH 6.5-9.0 |

Mixed Solution Composition Example 6

| | | | | | |
|---|---|---|---|---|---|
| A (mL/L) | 0 | 30 | 50 | 80 | 100 |
| B (mL/L) | | | 25 | | |
| Na⁺ (mM) | | | 132 | | |
| $Mg^{2+}$ (mM) | 0.250 | 0.346 | 0.410 | 0.506 | 0.570 |
| $Ca^{2+}$ (mM) | 0.95 | 1.25 | 1.45 | 1.75 | 1.95 |
| $Cl^-$ (mM) | 94.4 | 95.2 | 95.7 | 96.5 | 97.0 |
| Lactate (mM) | | | 40 | | |
| Glucose (mM) | 0 | 83.3 | 138.8 | 222.0 | 278 |

Example 7

| Concentrate A7 | |
|---|---|
| Glucose | 2.775M |
| Calcium chloride | 0.015M |
| Magnesium chloride | 0.007M |
| Hydrochloric acid | ad. pH 2.0-3.2 |
| Concentrate B7 | |
| Sodium chloride | 3.68M |
| Calcium chloride | 0.06M |
| Magnesium chloride | 0.0015M |
| Sodium lactate | 1.60M |
| Sodium hydroxide | ad. pH 6.5-9.0 |

Mixed Solution Composition Example 7

| | | | | | |
|---|---|---|---|---|---|
| A (mL/L) | 0 | 30 | 50 | 80 | 100 |
| B (mL/L) | | | 25 | | |
| Na⁺ (mM) | | | 132 | | |
| $Mg^{2+}$ (mM) | 0.050 | 0.260 | 0.400 | 0.610 | 0.750 |
| $Ca^{2+}$ (mM) | 1.25 | 1.57 | 1.78 | 2.09 | 2.30 |
| $Cl^-$ (mM) | 94.6 | 95.7 | 96.4 | 97.4 | 98.1 |
| Lactate (mM) | | | 40 | | |
| Glucose (mM) | 0 | 83.3 | 138.8 | 222.0 | 278 |

Example 8

| Concentrate A8 | |
|---|---|
| Glucose | 2.775M |
| Hydrochloric acid | ad. pH 2.0-3.2 |
| Concentrate B8 | |
| Sodium chloride | 1.84M |
| Potassium chloride | 0.08M |
| Calcium chloride | 0.035M |
| Magnesium chloride | 0.010M |
| Sodium lactate | 0.80M |
| Sodium hydroxide | ad. pH 6.5-9.0 |

Mixed Solution Composition Example 8

| | | | | | |
|---|---|---|---|---|---|
| A (mL/L) | 0 | 30 | 50 | 80 | 100 |
| B (mL/L) | | | 50 | | |
| Na$^+$ (mM) | | | 132 | | |
| K$^+$ (mM) | | | 4 | | |
| Mg$^{2+}$ (mM) | | | 0.50 | | |
| Ca$^{2+}$ (mM) | | | 1.75 | | |
| Cl$^-$ (mM) | | | 100.5 | | |
| Lactate (mM) | | | 40.0 | | |
| Glucose (mM) | 0 | 83.3 | 138.8 | 222.0 | 278 |

Example 9

| Concentrate A9 | |
|---|---|
| Glucose | 2.775M |
| Hydrochloric acid | ad. pH 2.0-3.2 |
| Concentrate B9 | |
| Sodium chloride | 2.76M |
| Calcium chloride | 0.053M |
| Magnesium chloride | 0.015M |
| Sodium lactate | 1.20M |
| Tri-sodium citrate | 0.0075M |
| Sodium hydroxide | ad. pH 6.5-9.0 |

Mixed Solution Composition Example 9

| | | | | | |
|---|---|---|---|---|---|
| A (mL/L) | 0 | 30 | 50 | 80 | 100 |
| B (mL/L) | | | 33.14 | | |
| Na$^+$ (mM) | | | 132 | | |
| Mg$^{2+}$ (mM) | | | 0.497 | | |
| Ca$^{2+}$ (mM) | | | 1.74 | | |
| Cl$^-$ (mM) | | | 95.9 | | |
| Lactate (mM) | | | 39.8 | | |
| Glucose (mM) | 0 | 83.3 | 138.8 | 222.0 | 278.0 |
| Citrate (mM) | | | 0.249 | | |

Example 10

| Concentrate A10 | |
|---|---|
| Glucose | 2.775M |
| Sodium chloride | 0.01M |
| Hydrochloric acid | ad. pH 2.0-3.2 |
| Concentrate B10 | |
| Sodium chloride | 2.76M |
| Calcium chloride | 0.052M |
| Magnesium chloride | 0.0075M |
| Sodium lactate | 1.20M |
| Sodium hydroxide | ad. pH 6.5-9.0 |

Mixed Solution Composition Example 10

| | | | | | |
|---|---|---|---|---|---|
| A (mL/L) | 0 | 30 | 50 | 80 | 100 |
| B (mL/L) | | | 33.34 | | |
| Na$^+$ (mM) | 132.0 | 132.3 | 132.5 | 132.8 | 133.0 |
| Mg$^{2+}$ (mM) | | | 0.25 | | |
| Ca$^{2+}$ (mM) | | | 1.75 | | |
| Cl$^-$ (mM) | 96.0 | 96.3 | 96.5 | 96.8 | 97 |
| Lactate (mM) | | | 40 | | |
| Glucose (mM) | 0 | 83.3 | 138.8 | 222.0 | 278 |

Example 11

| Concentrate A11 | |
|---|---|
| Glucose | 3.885M |
| Hydrochloric acid | ad. pH 2.0-3.2 |
| Concentrate B11 | |
| Sodium chloride | 2.76M |
| Calcium chloride | 0.053M |
| Magnesium chloride | 0.015M |
| Sodium lactate | 1.20M |
| Sodium hydroxide | ad. pH 6.5-9.0 |

Mixed Solution Composition Example 11

| | | | | | |
|---|---|---|---|---|---|
| A (mL/L) | 0 | 21.4 | 35.7 | 57.1 | 71.4 |
| B (mL/L) | | | 33.3 | | |
| Na$^+$ (mM) | | | 131.9 | | |
| Mg$^{2+}$ (mM) | | | 0.50 | | |
| Ca$^{2+}$ (mM) | | | 1.75 | | |
| Cl$^-$ (mM) | | | 96.4 | | |
| Lactate (mM) | | | 40.0 | | |
| Glucose (mM) | 0 | 83.1 | 138.7 | 221.8 | 277.4 |

Example 12

| Concentrate A12 | |
|---|---|
| Glucose | 2.775M |
| Calcium chloride | 0.015M |
| Magnesium chloride | 0.007M |
| Hydrochloric acid | ad. pH 2.0-3.2 |
| Concentrate B12 | |
| Sodium chloride | 2.74M |
| Calcium chloride | 0.030M |
| Magnesium chloride | 0.0020M |
| Sodium lactate | 1.20M |
| Tri-sodium citrate | 0.0075M |
| Sodium hydroxide | ad. pH 6.5-9.0 |

Mixed Solution Composition Example 12

| | | | | | |
|---|---|---|---|---|---|
| A (mL/L) | 0 | 21.4 | 35.7 | 57.1 | 71.4 |
| B (mL/L) | | | 33.3 | | |
| Na$^+$ (mM) | | | 132 | | |

-continued

| | | | | | |
|---|---|---|---|---|---|
| $Mg^{2+}$ (mM) | 0.05 | 0.20 | 0.30 | 0.45 | 0.55 |
| $Ca^{2+}$ (mM) | 1.0 | 1.32 | 1.54 | 1.86 | 2.07 |
| $Cl^-$ (mM) | 93.4 | 94.4 | 95.0 | 95.9 | 96.6 |
| Lactate (mM) | | | 40 | | |
| Glucose (mM) | 0 | 59.4 | 99.1 | 158.5 | 198.1 |
| Citrate (mM) | | | 0.25 | | |

Example 13

| Concentrate A13 | |
|---|---|
| Glucose | 2.775M |
| Hydrochloric acid | ad. pH 2.0-3.2 |
| Concentrate B13 | |
| Sodium chloride | 1.84M |
| Calcium chloride | 0.05M |
| Magnesium chloride | 0.01M |
| Sodium hydroxide | ad. pH 6.5-9.0 |
| Concentrate C13 | |
| Sodium chloride | 1.84M |
| Sodium lactate | 1.60M |
| Sodium hydroxide | ad. pH 6.5-9.0 |

Mixed Solution Composition Example 13

| | | | | | |
|---|---|---|---|---|---|
| A (mL/L) | 10 | 27.2 | 45.4 | 77.2 | 100 |
| B (mL/L) | | | 25 | | |
| C (mL/L) | 15.7 | 18.6 | 21.51 | 24.42 | 25 |
| $Na^+$ (mM) | 100 | 110 | 120 | 130 | 132 |
| $Mg^{2+}$ (mM) | | | 0.25 | | |
| $Ca^{2+}$ (mM) | | | 1.25 | | |
| $Cl^-$ (mM) | 77.9 | 83.2 | 88.6 | 93.9 | 95.0 |
| Lactate (mM) | 25.12 | 29.8 | 34.4 | 39.0 | 40.0 |
| Glucose (mM) | 27.8 | 75.5 | 126 | 214.2 | 277.5 |

Example 14

| Concentrate A14 | |
|---|---|
| Glucose | 2.775M |
| Hydrochloric acid | ad. pH 2.0-3.2 |
| Concentrate B14 | |
| Sodium chloride | 1.84M |
| Calcium chloride | 0.05M |
| Magnesium chloride | 0.01M |
| Sodium hydroxide | ad. pH 6.5-9.0 |
| Concentrate C14 | |
| Sodium chloride | 0.80M |
| Sodium bicarbonate | 0.70M |
| Sodium hydroxide | ad. pH 6.5-9.0 |

Mixed Solution Composition Example 14

| | | | | | |
|---|---|---|---|---|---|
| A (mL/L) | 10 | 27.2 | 45.4 | 77.2 | 100 |
| B (mL/L) | | | 25 | | |
| C (mL/L) | | | 57.1 | | |
| $Na^+$ (mM) | | | 131.7 | | |
| $Mg^{2+}$ (mM) | | | 0.25 | | |
| $Ca^{2+}$ (mM) | | | 1.25 | | |
| $Cl^-$ (mM) | | | 94.7 | | |
| Bicarbonate (mM) | | | 40 | | |
| Glucose (mM) | 27.8 | 75.5 | 126 | 214.2 | 277.5 |

Example 15

| Concentrate A15 | |
|---|---|
| Glucose | 2.775M |
| Hydrochloric acid | ad. pH 2.0-3.2 |
| Concentrate B15 | |
| Sodium chloride | 1.84M |
| Calcium chloride | 0.0526M |
| Magnesium chloride | 0.015M |
| Sodium hydroxide | ad. pH 6.5-9.0 |
| Concentrate C15 | |
| Sodium chloride | 1.0M |
| Sodium lactate | 0.28M |
| Sodium bicarbonate | 0.70M |
| Sodium hydroxide | ad. pH 6.5-9.0 |

Mixed Solution Composition Example 15

| | | | | | |
|---|---|---|---|---|---|
| A (mL/L) | 0 | 30 | 50 | 80 | 100 |
| B (mL/L) | | | 33.3 | | |
| C (mL/L) | | | 35.7 | | |
| $Na^+$ (mM) | | | 132 | | |
| $Mg^{2+}$ (mM) | | | 0.50 | | |
| $Ca^{2+}$ (mM) | | | 1.75 | | |
| $Cl^-$ (mM) | | | 101.5 | | |
| Lactate (mM) | | | 10 | | |
| Bicarbonate (mM) | | | 25 | | |
| Glucose (mM) | 0 | 83.3 | 138.8 | 222 | 277.5 |

Example 16

| Concentrate A16 | |
|---|---|
| Glucose | 2.775M |
| Hydrochloric acid | ad. pH 2.0-3.2 |
| Concentrate B16 | |
| Sodium chloride | 2.76M |
| Calcium chloride | 0.060M |
| Magnesium chloride | 0.024M |
| Sodium lactate | 1.20M |
| Sodium hydroxide | ad. pH 6.5-9.0 |
| Concentrate C16 | |
| Sodium chloride | 3.31M |
| Sodium bicarbonate | 0.70M |
| Sodium hydroxide | ad. pH 6.5-9.0 |

Mixed Solution Composition Example 16

| | | | | | |
|---|---|---|---|---|---|
| A (mL/L) | 0 | 30 | 50 | 80 | 100 |
| B (mL/L) | | | 20.83 | | |
| C (mL/L) | | | 14.3 | | |
| $Na^+$ (mM) | | | 132 | | |
| $Mg^{2+}$ (mM) | | | 0.50 | | |
| $Ca^{2+}$ (mM) | | | 1.25 | | |
| $Cl^-$ (mM) | | | 108 | | |

-continued

| | | | | |
|---|---|---|---|---|
| Lactate (mM) | | 25 | | |
| Bicarbonate (mM) | | 10 | | |
| Glucose (mM) | 0 | 83.3 | 138.8 | 222 | 277.5 |

Example 17

| Concentrate A17 | |
|---|---|
| Glucose | 2.775M |
| Hydrochloric acid | ad. pH 2.0-3.2 |
| Concentrate B17 | |
| Sodium chloride | 2.694M |
| Calcium chloride | 0.120M |
| Magnesium chloride | 0.020M |
| Sodium lactate | 1.20M |
| Sodium hydroxide | ad. pH 6.5-9.0 |
| Concentrate C17 | |
| Sodium chloride | 2.694M |
| Sodium bicarbonate | 0.70M |
| Sodium hydroxide | ad. pH 6.5-9.0 |

Mixed Solution Composition Example 17

| | | | | | |
|---|---|---|---|---|---|
| A (mL/L) | 0 | 30 | 50 | 80 | 100 |
| B (mL/L) | | | 12.5 | | |
| C (mL/L) | | | 21.4 | | |
| Na+ (mM) | | | 132 | | |
| Mg2+ (mM) | | | 0.250 | | |
| Ca2+ (mM) | | | 1.50 | | |
| Cl− (mM) | | | 94.8 | | |
| Lactate (mM) | | | 15 | | |
| Bicarbonate (mM) | | | 15 | | |
| Glucose (mM) | 0 | 83.3 | 138.8 | 222 | 277.5 |

Example 18

| Concentrate A18 30% glucose | |
|---|---|
| Glucose | 1.665M |
| Hydrochloric acid | ad. pH 2.0-3.2 |
| Concentrate B18 35X | |
| Sodium chloride | 3.68M |
| Calcium chloride | 0.07M |
| Magnesium chloride | 0.02M |
| Sodium lactate | 1.60M |
| Sodium hydroxide | ad. pH 6.5-9.0 |

Mixed Solution Composition Example 18

| | | | | | |
|---|---|---|---|---|---|
| A (mL/L) | 0 | 50 | 83.3 | 133.3 | 167 |
| B (mL/L) | | | 25 | | |
| Na+ (mM) | | | 132 | | |
| Mg2+ (mM) | | | 0.50 | | |
| Ca2+ (mM) | | | 1.75 | | |
| Cl− (mM) | | | 96.5 | | |
| Lactate (mM) | | | 40 | | |
| Glucose (mM) | 0 | 83.3 | 138.7 | 222.0 | 278 |

Example—Water Activity

The following Example 19—were made for investigating the water activity of the first concentrate and the second concentrate.

The water activity of the peritoneal dialysis fluid according to the present invention has been measured, at 25° C. (according to DCC-307014, ver. 1.0)

Example 19

Concentrate A19:
50% glucose (anhydrous)
pH adjusted with HCl to 2.4-2.8
The concentrate was prepared for dilution 20×.
The water activity $a_w$=0.92
(was measured before and after heat sterilization).

| Concentrate B19 | |
|---|---|
| sodium chloride | 3.68M |
| magnesium chloride | 10 mM |
| calcium chloride | 54 mM |
| sodium lactate | 1.6M |
| pH | 7.5 |

Water activity $a_w$=0.75
(was measured before and after heat sterilization).

Example 20—Comparative Example

The first concentrate was compared with Concentrate 1 as described in U.S. Pat. No. 5,344,392.
Concentrate 1
Concentrate 1 has the following composition:

| | |
|---|---|
| sodium chloride | 11.34 g/100 ml |
| sodium lactate | 7.84 g/100 ml |
| calcium chloride | 514 mg/100 ml |
| magnesium chloride | 304 mg/100 ml, | adjusted to a pH of approximately 6.4.
The water activity of the Concentrate 1 was measured, $a_w$=0.90.

Example 21

Test fluids representing candidate concentrates were prepared by adding different amounts of solid constituents as defined to containers and finally adding purified water up to a desired volume. The test solution was heat sterilized and incubated for more than two months at +4° C. The ready-to-use peritoneal dialysis fluid based on the first concentrate and second concentrate is also presented.
X (Corresponds to Second Concentrate)

| | |
|---|---|
| Sodium chloride | 2.76M |
| Calcium chloride | 0.0375M |
| Magnesium chloride | 0.0075M |
| Sodium lactate | 1.20M |
| Sodium hydroxide | Ad. pH 6.8-9.0 |

Y 50% Glucose (Corresponds to First Concentrate)

| | |
|---|---|
| Glucose | 2.775M |
| Hydrochloric acid | Ad. pH 2.0-3.1 |

Mixed Solution Composition Example 21

| | | | | | |
|---|---|---|---|---|---|
| Y (mL/L) | 0 | 30 | 50 | 80 | 100 |
| X (mL/L) | | | 33.3 | | |
| $Na^+$ (mM) | | | 132 | | |
| $Mg^{2+}$ (mM) | | | 0.25 | | |
| $Ca^{2+}$ (mM) | | | 1.25 | | |
| $Cl^-$ (mM) | | | 96 | | |
| Lactate (mM) | | | 40 | | |
| Glucose (mM) | 0 | 83.3 | 138.8 | 222.0 | 278 |

Concentration of Calcium in final ready-to-use dialysis fluid is 1.75 mM.

Precipitations were not found in X (corresponding to the second concentrate).

Example 22

X (Corresponding to Second Concentrate)

| | |
|---|---|
| Sodium chloride | 2.3M |
| Calcium chloride | 0.04375M |
| Magnesium chloride | 0.00625M |
| Sodium lactate | 1.00M |
| Sodium hydroxide | ad. pH 6.8-9.0 |

Y: 50% Glucose (Corresponds to First Concentrate)

| | |
|---|---|
| Glucose | 2.775M |
| Hydrochloric acid | Ad. pH 2.0-3.1 |

Mixed Solution Composition Example 22

| | | | | | |
|---|---|---|---|---|---|
| Y (mL/L) | 0 | 30 | 50 | 80 | 100 |
| X (mL/L) | | | 40 | | |
| $Na^+$ (mM) | | | 132 | | |
| $Mg^{2+}$ (mM) | | | 0.25 | | |
| $Ca^{2+}$ (mM) | | | 1.75 | | |
| $Cl^-$ (mM) | | | 96 | | |
| Lactate (mM) | | | 40 | | |
| Glucose (mM) | 0 | 83.3 | 138.8 | 222.0 | 278 |

Concentration of Calcium in final ready-to-use dialysis fluid is 1.75 mM.

Precipitations were not found in A (corresponding to the second concentrate).

Examples 23-29—pH of the Peritoneal Dialysis Fluid

Test fluids representing candidate concentrates were prepared by adding different amounts of solid constituents as defined to containers and finally adding purified water up to a desired volume. pH of the test fluids was measured. pH of the obtained ready-to-use peritoneal dialysis fluid based on the first concentrate and second concentrate is also presented is presented in the tables.

Example 23

Concentrates A23:1-5 were prepared with varying glucose content and varying pH.
Concentrates B23:1-5, lactate containing buffer, dilution 40×, with final concentration (i.e. as in the ready-to-use fluid) of calcium of 1.25 mM, were prepared with varying pH. pH were measured. Results are presented in table:

| | Glucose concentration | | | | |
|---|---|---|---|---|---|
| Concentrates in mix | 0% | 1.36% | 2.27% | 3.86% | 5% |
| 1. A pH 2.1 + B 40X pH 7.5, 1.25 mM Ca | 7.06 | 6.2 | 5.97 | 5.77 | 5.67 |
| 2. A pH 2.1 + B 40X pH 9.0, 1.25 mM Ca | 7.21 | 6.23 | 6 | 5.77 | 5.65 |
| 3. A pH 2.6 + B 40X pH 7.5, 1.25 mM Ca | 7.06 | 6.76 | 6.62 | 6.45 | 6.37 |
| 4. A pH 3.2 + B 40X pH 8.0, 1.25 mM Ca | 7.2 | 6.76 | 6.65 | 6.48 | 6.4 |
| 5. A pH 2.6 + B 40X pH 8.0, 1.25 mM Ca | 7.2 | 6.59 | 6.38 | 6.2 | 6.07 |

Example 24

Concentrates A24:1-4 were prepared with varying glucose content, with constant pH 3.0.
Concentrates B24:1-4, lactate containing buffer, dilution 40×, with final concentration of calcium of 1.25 mM, varying concentration of citrate (defined with amounts in concentrate), varying pH. pH were measured. Results are presented in table:

| | Glucose concentration | | | | |
|---|---|---|---|---|---|
| Concentrates in mix | 0% | 1.36% | 2.27% | 3.86% | 5% |
| 1. A pH 3.0 + B 40X pH 7.5, 0 mM Citrate, 1.25 mM Ca | 7.10 | 6.60 | — | 6.36 | — |
| 2. A pH 3.0 + B 40X pH 7.5, 1 mM Citrate, 1.25 mM Ca | 7.18 | 6.68 | — | 6.38 | — |
| 3. A pH 3.0 + B 40X pH 7.5, 5 mM Citrate, 1.25 mM Ca | 7.14 | 6.73 | — | 6.41 | — |
| 4. A pH 3.0 + B 40X pH 7.5, 10 mM Citrate, 1.25 mM Ca | 7.24 | 6.80 | — | 6.46 | — |

Example 25

Concentrates A25:1-5 were prepared with varying glucose content, with constant pH 3.0.
Concentrates B25:1-5, lactate containing buffer, varying dilution 10×-40×, with final concentration of calcium of 1.25 mM, pH 7.5. pH of the fluids were measured and the results are presented in table:

| | Glucose concentration | | | | |
|---|---|---|---|---|---|
| Concentrates in mix | 0% | 1.36% | 2.27% | 3.86% | 5% |
| 1. A pH 3.0 + B 40X pH 7.5, 1.25 mM Ca | 7.14 | 6.75 | — | 6.44 | 6.35 |
| 2. A pH 3.0 + B 30X pH 7.5, 1.25 mM Ca | 6.83 | 6.31 | — | 5.80 | 5.68 |
| 3. A pH 3.0 + B 20X pH 7.5, 1.25 mM Ca | 6.58 | 5.66 | — | 5.14 | 5.01 |
| 4. A pH 3.0 + B 10X pH 7.5, 1.25 mM Ca | 6.58 | 5.31 | — | 4.69 | 4.50 |

-continued

| Concentrates in mix | Glucose concentration | | | | |
|---|---|---|---|---|---|
| | 0% | 1.36% | 2.27% | 3.86% | 5% |
| 5. A pH 3.0 + B 40X pH 7.5, 1.25 mM Ca | 7.14 | 6.75 | — | 6.44 | 6.35 |

Example 26

Concentrates A26:1-2 were prepared with varying glucose content, with constant pH 3.0.

Concentrates B26:1-2, lactate containing buffer, dilution 40×, pH 7.5, Calcium concentration to provide 1.25 mM in ready-to-use dialysis fluid, and varying citrate concentration (defined with amount citrate in concentrate). pH of the fluids were measured and the results are presented in table:

| Concentrates in mix | Glucose concentration | | | | |
|---|---|---|---|---|---|
| | 0% | 1.36% | 2.27% | 3.86% | 5% |
| 1. A pH 3.0 + B 40x pH 7.5, 5 mM Citrate, 1.25 mM Ca | 6.97 | 6.76 | — | 6.53 | 6.41 |
| 2. A pH 3.0 + B 40x pH 7.5, 10 mM Citrate, 1.25 mM Ca | 6.81 | 6.64 | — | 6.54 | 6.46 |

Example 27

Concentrates A27:1-4 were prepared with varying glucose content and pH 3.0.

Concentrates B27:1-4, lactate containing buffer, varying dilution 10×-40×, with final concentration of calcium of 1.25 mM, were prepared with pH 7.5. pH were measured with the results presented in table:

| Concentrates in mix | Glucose concentration | | | | |
|---|---|---|---|---|---|
| | 0% | 1.36% | 2.27% | 3.86% | 5% |
| 1. A pH 3.0 + B 40X pH 7.5, 1.25 mM Ca | 7.01 | 6.72 | — | 6.45 | 6.4 |
| 2. A pH 3.0 + B 30X pH 7.5, 1.25 mM Ca | 6.5 | 6.1 | — | 5.75 | 5.74 |
| 3. A pH 3.0 + B 20X pH 7.5, 1.25 mM Ca | 6.1 | 5.46 | — | 5.07 | 4.98 |
| 4. A pH 3.0 + B 10X pH 7.5, 1.25 mM Ca | 6.09 | 5.14 | — | 4.6 | 4.52 |

Example 28

Concentrates A28:1-5 were prepared with varying glucose content and pH3.0.

Concentrates B28:1-5, lactate containing buffer, dilution 20×-35×, with final concentration of calcium of 1.75 mM, with 0 mM, 5.71 mM, 8.57 mM, and 10 mM citrate, pH 7.5. pH of the ready-to-use dialysis fluids were measured. Results are presented in the table:

| Concentrates in mix | Glucose concentration | | | | |
|---|---|---|---|---|---|
| | 0% | 1.36% | 2.27% | 3.86% | 5% |
| 1. A pH 3.0 + B 20x pH 7.5, 1.75 mM Ca | 6.92 | 6.69 | — | — | 6.34 |
| 2. A pH 3.0 + B 30x pH 7.5, 1.75 mM Ca | 6.88 | 6.64 | — | — | 6.35 |
| 3. A pH 3.0 + B 35x pH 7.5, 1.75 mM Ca | 6.90 | 6.68 | — | — | 6.35 |
| 4. A pH 3.0 + B 20x pH 7.5, 5.71 mM Citrate, 1.75 mM Ca | 7.03 | 6.77 | — | — | 6.43 |
| 5. A pH 3.0 + B 30x pH 7.5, 8.57 mM Citrate, 1.75 mM Ca | 7.02 | 6.79 | — | — | 6.45 |
| 6. A pH 3.0 + B 35x pH 7.5, 10 mM Citrate, 1.75 mM Ca | 6.97 | 6.77 | — | — | 6.42 |

Example 29

Concentrates A29:1-5 were prepared with varying glucose content and pH 3.0.

Concentrates B29:1-5, lactate containing buffer, for dilution 20×-30×, with final concentration of calcium of 1.75 mM, with 0 mM, and 10 mM citrate (included in the concentrate), pH 7.5 and pH 6.6, were prepared. pH of the ready-to-use dialysis fluids were measured. Results are presented in the table:

| Concentrates in mix | Glucose concentration | | | | |
|---|---|---|---|---|---|
| | 0% | 1.36% | 2.27% | 3.86% | 5% |
| 1. A pH 3.0 + B 30x pH 7.5, 1.75 mM Ca | 6.96 | 6.71 | 6.57 | 6.42 | 6.32 |
| 2. A pH 3.0 + B 25x pH 7.5, 1.75 mM Ca | 6.95 | 6.68 | 6.60 | 6.42 | 6.33 |
| 3. A pH 3.0 + B 20x pH 7.5, 1.75 mM Ca | 6.98 | 6.73 | 6.57 | 6.40 | 6.31 |
| 4. A pH 3.0 + B 20x pH 7.5, 10 mM Citrate, 1.75 mM Ca | 7.12 | 6.89 | 6.70 | 6.53 | 6.44 |
| 5. A pH 3.0 + B 20x pH 6.6, 1.75 mM Ca | 6.68 | 6.51 | 6.42 | 6.29 | 6.23 |

Example 30—pH Measurement After Terminal Sterilisation (Heat Sterilisation)

The first concentrates herein described were terminal sterilised by heat sterilisation. The variation of pH due to the sterilisation was investigated.

First concentrates comprising 50% and 60% glucose, with varying pH between 1.0 and 4.0, were tested. The result is presented in the following table:

| pH in PD concentrates before/after sterilization | | | |
|---|---|---|---|
| A concentrates | before | after | difference |
| A 50% (pH 1.0) | 1.04 | 1.09 | 0.05 |
| A 50% (pH 1.5) | 1.56 | 1.59 | 0.03 |
| A 50% (pH 2.0) | 2.04 | 2.04 | 0 |
| A 50% (pH 2.1) | 2.09 | 2.03 | −0.06 |
| A 50% (pH 2.5) | 2.48 | 2.47 | −0.01 |
| A 50% (pH 2.5) | 2.50 | 2.47 | −0.03 |
| A 50% (pH 2.5) | 2.50 | 2.54 | 0.04 |
| A 50% (pH 2.6) | 2.60 | 2.5 | −0.1 |
| A 50% (pH 3.0) | 2.97 | 2.90 | −0.07 |
| A 50% (pH 3.0) | 3.00 | 2.93 | −0.07 |
| A 50% (pH 3.0) | 3.00 | 2.99 | −0.01 |
| A 50% (pH 3.16) | 3.16 | 3.06 | −0.1 |

-continued pH in PD concentrates before/after sterilization

| A concentrates | before | after | difference |
|---|---|---|---|
| A 50% (pH 3.2) | 3.14 | 2.93 | −0.21 |
| A 50% (pH 3.5) | 3.57 | 3.31 | −0.26 |
| A 50% (pH 4.0) | 4.03 | 3.51 | −0.52 |
| A 60% (pH 2.5) | 2.50 | 2.60 | 0.10 |
| A 60% (pH 3.0) | 3.00 | 3.03 | 0.03 |

Example 31

The second concentrates herein described was terminal sterilised by heat sterilisation. The variation of pH due to the sterilisation was investigated.
Second concentrates suitable for dilution 10×, 20×, 30×, and 40×, aiming for pH 6.6, 7.5, 8.0, 9.0, comprising Calcium to provide 1.25 mM or 1.75 mM Calcium in ready-to-use dialysis fluid, and 0 mM, 1 mM, 5 mM, 5.71 mM, 8.57 mM, and 10 mM citrate were tested. The result is presented in the following table:

| B concentrates | before | after | difference |
|---|---|---|---|
| B 10X (pH 7.5), 1.25 mM Ca | 7.56 | 7.27 | −0.29 |
| B 10X (pH 6.6), 1.25 mM Ca | 6.65 | 6.49 | −0.16 |
| B 10X (pH 7.5), 1.25 mM Ca | 7.43 | 6.89 | −0.54 |
| B 20X (pH 7.5), 1.25 mM Ca | 7.43 | 7.14 | −0.29 |
| B 20X (pH 6.6), 1.25 mM Ca | 6.60 | 6.46 | −0.14 |
| B 20X (pH 7.5), 1.25 mM Ca | 7.52 | 6.74 | −0.78 |
| B 20X (pH 7.5), 1.75 mM Ca | 7.49 | 7.26 | −0.23 |
| B 20X (pH 7.5), 1.75 mM Ca, 5.71 mM Na-cit | 7.52 | 7.29 | −0.23 |
| B 30X (pH 7.5), 1.25 mM Ca | 7.64 | 7.36 | −0.28 |
| B 30X (pH 6.6), 1.25 mM Ca | 6.59 | 6.5 | −0.09 |
| B 30X (pH 7.5), 1.25 mM Ca | 7.57 | 7.2 | −0.37 |
| B 30X (pH 7.5), 1.75 mM Ca | 7.55 | 7.04 | −0.51 |
| B 30X (pH 7.5), 1.75 mM Ca, 8.57 mM Na-cit | 7.53 | 7.29 | −0.24 |
| B 35X (pH 7.5), 1.75 mM Ca | 7.54 | 7.24 | −0.30 |
| B 35X (pH 7.5), 1.75 mM Ca, 10 mM Na-cit | 7.52 | 7.23 | −0.29 |
| B 40X (pH 7.5), 1.25 mM Ca | 7.51 | 7.15 | −0.36 |
| B 40X (pH 8.0), 1.25 mM Ca | 7.99 | 7.37 | −0.62 |
| B 40X (pH 9.0), 1.25 mM Ca | 8.96 | 7.79 | −1.17 |
| B 40X (pH 6.6), 1.25 mM Ca | 6.60 | 6.51 | −0.09 |
| B 40X (pH 7.5), 1.25 mM Ca | 7.49 | 7.32 | −0.17 |
| B 40X (pH 7.5), 1.25 mM Ca | 7.52 | 7.24 | −0.28 |
| B 40X (pH 7.5), 1.25 mM Ca, 1 mM Na-cit | 7.55 | 7.43 | −0.12 |
| B 40X (pH 6.6), 1.25 mM Ca, 5 mM Na-cit | 6.59 | 6.51 | −0.08 |
| B 40X (pH 7.5), 1.25 mM Ca, 5 mM Na-cit | 7.54 | 7.34 | −0.2 |
| B 40X (pH 7.5), 1.25 mM Ca, 5 mM Na-cit | 7.51 | 7.14 | −0.37 |
| B 40X (pH 6.6), 1.25 mM Ca, 10 mM Na-cit | 6.59 | 6.51 | −0.08 |
| B 40X (pH 7.5), 1.25 mM Ca, 10 mM Na-cit | 7.54 | 7.35 | −0.19 |
| B 40X (pH 7.5), 1.25 mM Ca, 10 mM Na-cit | 7.50 | 7.25 | −0.25 |

It can be concluded that pH of the second concentrate decreases during the sterilisation While the invention has been described in connection with what is presently considered to be the most practical embodiments, it is to be understood that the invention is not to be limited to the disclosed embodiments, but on the contrary, is intended to cover various modifications and equivalents included within the spirit and the scope of the appended claims.

Example 32

Figure 3:
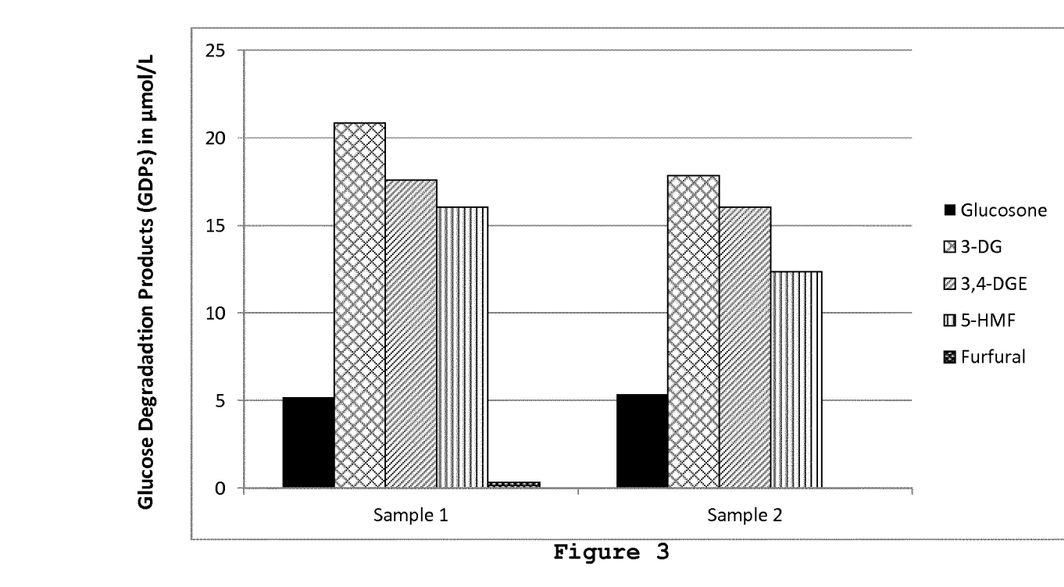
FIG. 3 shows the concentration of glucose degradation products in µmol/l which were determined according to Example 32 by UPLC/UV in the reconstituted and sterilized peritoneal solution of a first and second concentrate according to the invention (duplicate analysis, Sample 1 and 2) consisting of (per 100 mL of solution): 4.25 g glucose, 538 mg sodium chloride, 448 mg sodium lactate, 18.3 mg calcium chloride dihydrate, 5.08 mg magnesium chloride hexahydrate and water. The abbreviations used are identified in FIG. 2. In comparison to average GDP concentrations found in comparable state of the art products, see Himmele et al. (2012), the GDP concentrations in solutions based on a system as claimed herein are significantly lower.

A ready to use peritoneal solution was prepared from concentrates according to the invention and had a final content of (per 100 mL of solution) 4.25 g glucose, 538 mg sodium chloride, 448 mg sodium lactate, 18.3 mg calcium chloride dihydrate, 5.08 mg magnesium chloride hexahydrate and water. The pH of the solution was 6.3. Levels of 10 Glucose Degradation Products (GDP) were measured using a total of three validated methods. UPLC/UV was used for the determination of residual 5-hydroxymethyl Furfural (5-HMF) and Furfural. The method did not make use of any derivatization. UPLC/UV was also used for the determination of Glucosone, Glyoxal, Methylglyoxal, 3-deoxyglucosone (3-DG), 3-deoxygalactasone (3-DGal) and 3,4-di-deoxyglucosone-3-ene (3,4-DGE, and this method relied on derivatisation with 1,2 phenylenediamine to yield an ultraviolet-detectable molecule. UPLC/UV was used for the determination of acetaldehyde and formaldehyde, wherein this method relied on derivatisation with 2,4-dinitrophenylhydrazine to yield an ultraviolet-detectable molecule. It was found that the concentrations (in µmol/L) of 3-DGal, GO, formaldehyde and acetaldehyde were below the quantification limit. Furfural was above the quantification limit in one of the two tests performed for the above solution. The buffer concentrate, which was diluted accordingly (no glucose contained) was also tested for the existence of GDPs. No GDPs could be detected in the buffer solution. The detected concentrations of GDP are displayed in FIG. 3. Glucosone was detected in a concentration of 5.200 and 5.383 µmol/L in the two samples which were tested. 3-DG was detected in a concentration of 20.840 and 17,863 µmol/L, respectively. 3,4-DGE was detected in a concentration of 17.595 and 16.043 µM/L, respectively. 5-HMF was detected in a concentration of 16.061 and 12.365 µM/L, respectively. Finally, 0.345 µM/L furfural could be found in one of the two samples. In comparison to average GDP concentrations found in comparable state of the art products, see, for example, Himmele et al. (2012), Peritoneal Dialysis International, Vol. 32, p. 444-452, the GDP concentrations in solutions based on and prepared from concentrates as claimed herein are significantly lower. See, for example, Table 3 of Himmele et al (2012).

The invention claimed is:

1. A system for preparing a ready-to-use peritoneal dialysis fluid, the system comprising;
    a proportioning device connectable to a source of water;
    at least one source of first concentrate connectable to the proportioning device;
    at least one source of second concentrate connectable to the proportioning device; and optionally,
    at least one source of further concentrate connectable to the proportioning device,
    wherein said first concentrate comprises glucose at a concentration of 1.5 to 4 M and hydrochloric acid and has a pH of between 1.5 and 4, and wherein the first concentrate is free of buffer selected from acetate, lactate, citrate, pyruvate, carbonate, bicarbonate, and amino acid buffer, and free of electrolyte selected from sodium and potassium, and wherein the first concentrate is formulated for dilution with water at a ratio of 1:10 to 1:33; and
    wherein said second concentrate comprises a physiologically acceptable buffer which has a pH of between 5.5 and 9.0.

2. A system according to claim 1, wherein the first concentrate has a pH of between 2.0 and 3.5.

3. A system according to claim 1, wherein the first concentrate has a pH of between 2.2 and 3.0.

4. A system according to claim 1, wherein the second concentrate has a pH of between 6.0 and 8.5.

5. A system according to claim 1, wherein the physiologically acceptable buffer is selected from the group consisting of acetate, lactate, citrate, pyruvate, carbonate, bicarbonate, amino acid buffer, and mixtures thereof.

6. A system according to claim 1, wherein the physiologically acceptable buffer is lactate, bicarbonate or a mixture thereof.

7. A system according to claim 1, wherein the first concentrate further comprises at least one electrolyte selected from the group consisting of calcium, and magnesium.

8. A system according to claim 1, wherein the second concentrate further comprises at least one electrolyte selected from the group consisting of sodium, calcium, magnesium and potassium.

9. A system according to claim 1, wherein the system comprises at least one source of further concentrate, and wherein the further concentrate comprises at least one electrolyte selected from the group consisting of sodium, calcium, magnesium and potassium.

10. A system according to claim 1, wherein the further concentrate comprises a physiologically acceptable buffer selected from the group consisting of acetate, lactate, citrate, pyruvate, carbonate, bicarbonate, amino acid buffer, and mixtures thereof.

11. A system according to claim 1, wherein the first concentrate and the second concentrate each comprises calcium and the second concentrate comprises at least one further electrolyte selected from the group consisting of sodium, magnesium and potassium.

12. A system according to claim 1, wherein the second concentrate and the further concentrate each comprises calcium and at least one further electrolyte selected from the group consisting of sodium, magnesium and potassium.

13. A system according to claim 1, wherein the first concentrate and the second concentrate each comprises calcium and the second concentrate comprises at least one further electrolyte selected from the group consisting of sodium, magnesium and potassium, and wherein optionally the further concentrate comprises at least one electrolyte selected from the group consisting of sodium, calcium, magnesium and potassium.

14. A system according to claim 1, wherein the first concentrate and/or said second concentrate and/or said further concentrate are terminal sterilized.

15. A system according to claim 1, wherein the second concentrate is configured to be used for dilutions of between 1:10 and 1:40.

16. A system according to claim 1, wherein the second concentrate is configured to be used for dilutions of between 1:10 and 1:33.

17. A system according to claim 1, wherein the ready to use peritoneal dialysis fluid contains:
sodium ($Na^+$) 100-140 mM;
potassium ($K^+$) 0-4 mM;
calcium ($Ca^{2+}$) 0-2 mM;
magnesium ($Mg^{2+}$) 0-0.75 mM;
lactate 0-40 mM;
bicarbonate 0-35 mM; and
glucose 0-5%.

18. A system according to claim 1, wherein
optionally at least one of the first and second concentrate is terminal sterilized, and wherein the system is constructed to admix the first and second concentrates to form a ready to use peritoneal dialysis solution containing:
sodium ($Na^+$) 100-140 mM;
potassium ($K^+$) 0-4 mM;
calcium ($Ca^{2+}$) 0-2 mM;
magnesium ($Mg^{2+}$) 0-0.75 mM;
lactate 0-40 mM; and
glucose 0-5%.

19. A system according to claim 18, wherein the ready to use peritoneal dialysis solution contains:
sodium ($Na^+$) 132 mM;
potassium ($K^+$) 0-4 mM;
calcium ($Ca^{2+}$) 0.5-2 mM;
magnesium ($Mg^{2+}$) 0.25-0.50 mM;
lactate 0-40 mM; and
glucose 1.5-5%.

20. A system according to claim 19, wherein the ready to use peritoneal dialysis solution contains:
sodium ($Na^+$) 132 mM;
potassium ($K^+$) 0-4 mM;
calcium ($Ca^{2+}$) 1.25-1.75 mM;
magnesium ($Mg^{2+}$) 0.25-0.50 mM;
lactate 0-40 mM; and
glucose 1.5-5%.

21. A system according to claim 18, wherein the ready to use peritoneal dialysis solution comprises no lactate.

22. A system according to claim 18, wherein the ready to use peritoneal dialysis solution comprises 30 mM lactate.

23. A system according to claim 18, wherein the ready to use peritoneal dialysis solution comprises 40 mM lactate.

24. A system according to claim 1, wherein the first concentrate a pH less than 3.2.

25. A system according to claim 1, wherein said first concentrate has a conductivity of more than 100 µS/cm and a pH of between 1.5 and 3.

26. A system according to claim 1, wherein the first concentrate has a conductivity of more than 400 µS/cm and a pH of 2.3.

27. A system according to claim 1,
wherein the first concentrate has a pH of between 2.4 and 2.8, and
wherein the second concentrate comprises lactate, calcium, citrate, and optionally one or more electrolytes selected from the group consisting of sodium, magnesium, and potassium,
wherein the citrate is present in an amount giving stabilizing effect, and wherein the second concentrate has a pH of between 6.0 and 8.5.

28. A system according to claim 27, wherein the concentration of citrate is up to 10 mM.

29. A system according to claim 27, wherein the concentration of citrate is between 0.01 to 10 mM.

* * * * *